(12) United States Patent
Airoldi et al.

(10) Patent No.: US 6,511,700 B1
(45) Date of Patent: Jan. 28, 2003

(54) CVD DIAMOND BURRS FOR ODONTOLOGICAL AND RELATED USES

(75) Inventors: Vladimir Jesus Trava Airoldi, São José dos Campos (BR); Evaldo José Corat, São José dos Campos (BR); Nélia Ferriera Leite, São José dos Campos (BR); Edson Del Bosco, São José dos Campos (BR); Vitor Baranauskas, Campinas (BR); Marcia Carneiro Valera, São José dos Campos (BR); Angel Fidel Vilche Peña, Presidente Prudente (BR)

(73) Assignee: Instituto Nacional de Pesquisas Espacials, Sao Jose dos Campos (BR)

( * ) Notice: Subject to any disclaimer, the term of this patent is extended or adjusted under 35 U.S.C. 154(b) by 0 days.

(21) Appl. No.: 09/566,779

(22) Filed: May 5, 2000

Related U.S. Application Data

(60) Division of application No. 08/913,168, filed on Jan. 20, 1998, and a continuation of application No. 08/913,168, filed as application No. PCT/BR96/00008 on Feb. 15, 1996.

(30) Foreign Application Priority Data

Feb. 21, 1995 (BR) .............................................. 9500865

(51) Int. Cl.$^7$ ................................................ C23C 16/27
(52) U.S. Cl. .............. 427/2.29; 427/249.8; 427/249.11; 427/577
(58) Field of Search ................................ 427/2.29, 2.1, 427/249.8, 249.11, 577; 433/3, 165

(56) References Cited

U.S. PATENT DOCUMENTS

| | | | | |
|---|---|---|---|---|
| 4,526,542 A | * | 7/1985 | Kochis | 433/165 |
| 4,731,019 A | * | 3/1988 | Martin | 433/119 |
| 5,376,444 A | * | 12/1994 | Grotepass et al. | 428/336 |
| 5,782,638 A | * | 7/1998 | Warren, III et al. | 433/206 |
| 5,975,900 A | * | 11/1999 | Garman | 433/105 |

* cited by examiner

*Primary Examiner*—Bret Chen
(74) *Attorney, Agent, or Firm*—Darby & Darby

(57) ABSTRACT

A process for making CVD diamond burrs, mills and files of odontological and relates uses, for boring, abrading and machining teeth, glass, ceramics, metals, etc. A CVD diamond deposition method and gas mixture deposits a CVD diamond as a thin or thick film directly on the tool stick material, or as a freestanding film on a substrate material for later joining to a tool stick.

18 Claims, 1 Drawing Sheet

CVD DIAMOND BURRS FOR ODONTOLOGICAL AND RELATED USES

This is a division and continuation of application Ser. No. 08/913,168, filed Jan. 20, 1998 which is based on PCT/FR96/00008 filed Feb. 15, 1996. The prior application is hereby incorporated herein by reference, in its entirety.

This invention is related to the technology of Chemical Vapor Deposition (CVD) diamond growth. This is a subject of intense interest, not only due to basic research, but mainly to the many possible technological applications. Some of its superior properties make diamond the material of choice for many applications. Some CVD growth techniques have been developed at Instituto Nacional de Pesquisas Esnaciais (INPE) and the present invention is a result of this development.

An object of the invention is fundamented in the growth of thin and free standing CVD diamond films. These diamond films may be directly deposited and/or brazed on pins of stainless steel or any other material, to be used as burrs, mills and files in odontological and related work.

The diamond films may be obtained by the Hot Filament Chemical Vapor Deposition (HFCVD) or any other CVD technique. The HFCVD technique is particularly suitable due to its simplicity and low cost. Therefore we describe the obtainment of thin and free standing films based on the HFCVD technique. To use other growth techniques it is necessary to adapt the growth conditions to the appropriate activation method.

SUMMARY OF INVENTION

The procedure to obtain burr from thin and freestanding diamond films with poor adherence with the final burr stick is as follows:

a) preparation of substrate pins of a material suitable for diamond growth, molybdenum for example. The diameter and the length of such pins depend on the growth parameters and growth method. The upper end must be prepared to have the final form of the burr tip;

b) deposition of the diamond film on the upper end of the substrate pins prepared in the previous item. The growth conditions in the reactor for the deposition of the freestanding diamond tip must be adjusted in order to obtain the largest grain size. The boring and abrading capabilities depend on the grain size of the burr tip.

c) dissolution of the substrate pins in acid solution to release a freestanding diamond tip;

d) laser trimming of the diamond tip, or any other trimming method, to eliminate its fragile end;

e) brazing of the diamond tip on the final burr stick, made of stainless steel or any other suitable material, to obtain the final burr form. The excess of brazing alloy is removed to free the diamond cutting surface.

If the final burr stick is suitable for diamond growth with good film adherence, the procedure is as follows:

a) preparation of the burr stick in its final form;

b) preparation of the burr stick end surface to assure a good adherence of the diamond film;

c) deposition of a thin or thick diamond film directly on the burr stick end.

BRIEF DESCRIPTION OF THE DRAWINGS

Both cases may use the same diamond growth system during the deposition procedure. FIG. 1 shows a schematic diagram for a HFCVD diamond growth reactor. The method consists in flowing a gas mixture appropriate for diamond growth, for example a mixture of methane highly diluted (0.1–4%) in hydrogen, through the reactor: (1). The hot filament is located at the proper distance from the substrates (3). Each gas component of the mixture may be stored (4) and controlled independently with flow controllers (5). A premixed gas mixture may also be used. The reactor internal pressure may be conveniently controlled with needle valves (6), a vacuum pump (7), and an absolute pressure meter (8). The filament and substrate temperatures are monitored by an optical pyrometer (9) and a thermocouple, respectively. The film thickness may be controlled by the growth time.

With such reactor it is possible to grow diamond on various substrate forms depending on the desired application. For the case of odontological burrs the substrate may be small pins of which the upper ends are prepared to obtain the desired burr tip form. If the burr stick material is suitable for adherent film growth it is possible to grow a thin diamond film directly on the burr tip. Otherwise, if the burr stick is not suitable for diamond growth, it is necessary to grow a freestanding film on an appropriate substrate, dissolve the substrate, trim the fragile end of the diamond tip, and braze it on the burr stick.

Figure 1:
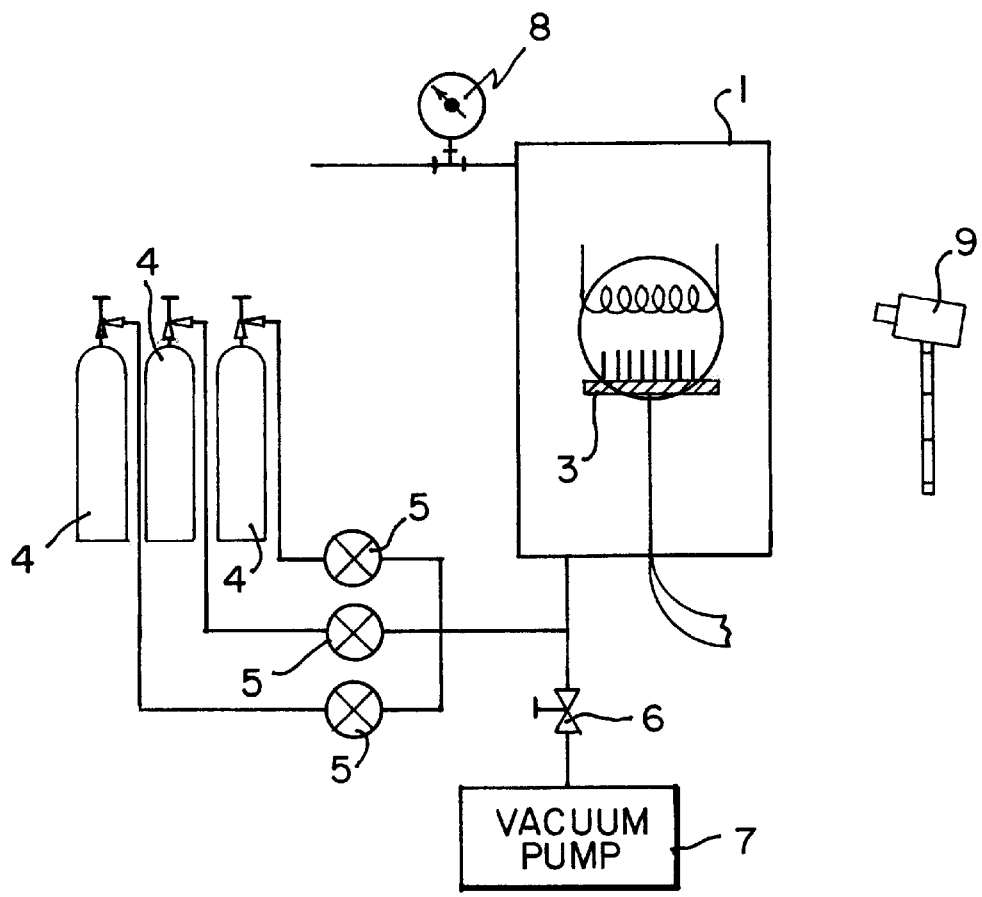
FIG. 1 is a schematic diagram of a HFCVD diamond growth reactor.
Figure 2:
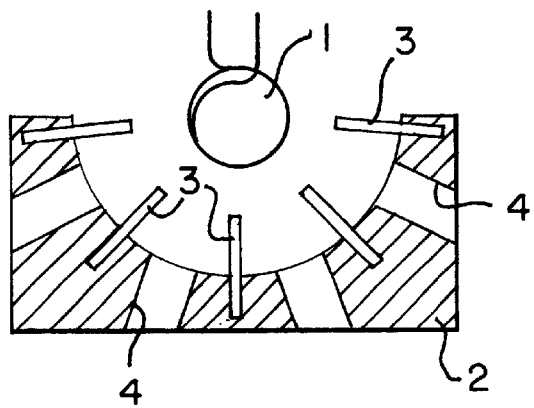
FIG. 2 is a substrate holder for an HFCVD system.

The HFCVD system is very convenient for scale production of such CVD diamond tips. An adequate substrates holder may maximize the production efficiency of a single reactor. FIG. 2 shows an example of an appropriate substrate holder positioned relative to the filament. A spiral filament (1) and the substrate holder (2) are placed in an adequate position to keep the same distance from the various pin substrates (3). The number of pin substrates per reactor may be in the order of several tens for filaments only a few centimeters long. The substrate holder may have through holes (4) conveniently distributed to allow gas flow in the reactive region.

What is claimed is:

1. A method of forming a diamond burr comprising the steps of:
   providing a substrate pin suitable for growth of a diamond film;
   preparing an end surface of said substrate pin in a form to permit growth of a diamond film to correspond to the desired final form of the burr diamond surface; and
   depositing a diamond film of the largest grain size effective for abrading by chemical vapor deposition (CVD) directly on said end surface with said deposited diamond film itself forming said diamond burr.

2. The method of claim 1 wherein said depositing step is carried out in a reactor under a mixture of methane gas and hydrogen.

3. The method of claim 2 wherein the methane gas is from 0.1–4.0 percent of the mixture.

4. The method of claim 2 wherein said step of depositing by CVD is carried out assisted by using one of radio frequency, microwave, hot filament, and arc jet plasma.

5. The method of claim 1 wherein said depositing step is carried out in a reactor in which pressure, temperature and gas mixture conditions are selected to maximize the grain size of said diamond film.

6. The method of claim 5 wherein said CVD process is carried out in the presence of a hot filament (HFCVD).

7. The method of claim 1 wherein said deposited diamond film forming said diamond burr is free standing on said substrate pin end surface and further comprising the steps of:

dissolving said substrate pin to release the diamond burr and affixing the diamond burr to a burr stick.

8. The method of claim 7 further comprising the step of trimming selected portions of said free standing diamond burr before affixing it to the burr stick.

9. The method of claim 7 wherein said affixing step comprises brazing said free standing diamond burr to said burr stick.

10. The method of claim 1 wherein said substrate pin comprises a burr stick part of a tool and the diamond burr is formed on an end surface of said substrate pin.

11. The method of claim 1 further comprising providing a plurality of said substrate pins each with a prepared end in a holder; and depositing by CVD said diamond film on said prepared end of each of said plurality of substrate pins substantially simultaneously.

12. Process for producing tools having diamond burrs, particularly for odontological purposes and related uses comprising the steps of:

a) providing a plurality of substrate pins of a material suitable for diamond film growth;

b) preparation of one end of each substrate pin to have a diamond film of a desired form of the diamond burr deposited thereon;

c) depositing a diamond film on said one end of each of said substrate pin in a reactor to grow a freestanding diamond burr thereon with the reactor growth conditions selected to obtain the largest grain size effective for abrading for the deposited diamond film;

d) dissolving the substrate pins in an acid solution to release a freestanding diamond burr from each substrate pin;

e) trimming a diamond burr if necessary to eliminate any undesired part of said diamond burr;

f) brazing or welding the diamond burr on a final burr stick to obtain the final tool.

13. Process according to claim 12, wherein the gas mixture contains methane diluted in hydrogen.

14. Process according to claim 13, wherein 0.1 to 4% methane is diluted in hydrogen.

15. Process according to claim 12, further comprising the step of controlling the diamond film thickness deposited by controlling the growth time.

16. Process according to claim 12, further comprising the step of providing a filament in said reactor and positioning the said one end of each of said plurality of substrate pins at a selected distance from said filament.

17. Process according to claim 16, further comprising using a substrate holder for holding several substrate pins and keeping the same distance between various substrate pins and said filament.

18. Process according to claim 16, further comprising providing through holes in the substrate holder to allow gas flow in said reactor through said through holes.

* * * * *

UNITED STATES PATENT AND TRADEMARK OFFICE
CERTIFICATE OF CORRECTION

PATENT NO.    : 6,511,700 B1
DATED         : January 28, 2003
INVENTOR(S)   : Vladmir J. Airoldi et al.

It is certified that error appears in the above-identified patent and that said Letters Patent is hereby corrected as shown below:

<u>Title page,</u>
Item [75], Inventors: delete "Nélia Ferriera Leite" and substitute
-- Nélia Ferreira Leite --

Signed and Sealed this

Fifteenth Day of April, 2003

JAMES E. ROGAN
*Director of the United States Patent and Trademark Office*